United States Patent
Ji et al.

(10) Patent No.: US 12,308,093 B2
(45) Date of Patent: *May 20, 2025

(54) METHOD AND DEVICE FOR IDENTIFYING SPECIFIC REGION IN MICROORGANISM TARGET FRAGMENT AND USE THEREOF

(71) Applicant: SHANGHAI ZJ BIO-TECH CO., LTD., Shanghai (CN)

(72) Inventors: Cong Ji, Shanghai (CN); Junbin Shao, Shanghai (CN); Yan Liu, Shanghai (CN); Xia Qi, Shanghai (CN); Yudan Jin, Shanghai (CN); Qiteng Li, Shanghai (CN)

(73) Assignee: SHANGHAI ZJ BIO-TECH CO., LTD, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/916,214

(22) PCT Filed: May 14, 2020

(86) PCT No.: PCT/CN2020/090180
§ 371 (c)(1),
(2) Date: Sep. 30, 2022

(87) PCT Pub. No.: WO2021/196358
PCT Pub. Date: Oct. 7, 2021

(65) Prior Publication Data
US 2023/0129284 A1    Apr. 27, 2023

(30) Foreign Application Priority Data

Apr. 2, 2020 (CN) .......................... 202010254403.4

(51) Int. Cl.
*G16B 30/10* (2019.01)
*G16B 35/20* (2019.01)
(52) U.S. Cl.
CPC ............. *G16B 30/10* (2019.02); *G16B 35/20* (2019.02)
(58) Field of Classification Search
CPC .................................. G16B 30/10; G16B 35/20
See application file for complete search history.

(56) References Cited

U.S. PATENT DOCUMENTS

2014/0235456 A1    8/2014 Garner, Jr.

FOREIGN PATENT DOCUMENTS

| CN | 101680872 A | 3/2010 |
| CN | 104919466 A | 3/2010 |
| CN | 105938522 A | 9/2016 |
| CN | 107463795 A | 12/2017 |
| CN | 108359692 A | 8/2018 |

OTHER PUBLICATIONS

Behr et al., 2016, Plos One, The Identification of Novel Diagnostic Marker Genes for the Detection of Beer Spoiling Pediococcus damnosus Strains Using the BIAst Diagnostic Gene finder, p. 1-12 (Year: 2016).*

Tu et al., Strain/species identification in metagenomes using genome-specific markers, 2014, Nucleic Acids Research, 42(8), p. 1-12 (Year: 2014).*

Johnson, Development of polymerase chain reaction-based assays for bacterial gene detection, 2000, Journal of Microbial Methods, 41, p. 201-209 (Year: 2000).*

* cited by examiner

*Primary Examiner* — Kaitlyn L Minchella
(74) *Attorney, Agent, or Firm* — IPRTOP LLC (57) ABSTRACT

A method for identifying presence of a microorganism in a sample has two processes. The first process comprises: S100, respectively comparing a microorganism target fragment with genome sequences of one or more comparison strain one-to-one, and removing fragments of which the similarity exceeds a preset value, to obtain a plurality of residual fragments as first-round cut fragments $T_1$-$T_n$; S200, respectively comparing the first-round cut fragments $T_1$-$T_n$ with the remaining comparison strains, and removing fragments of which the similarity exceeds a preset value, to obtain a collection of residual cut fragments as a candidate specific region of the microorganism target fragment; and S300, verifying and obtaining a specific region. The second process comprises performing a PCR amplification of the specific region to detect the microorganism. The method is high in accuracy and sensitivity, which can identify the subspecies level and a dual-verification module is provided.

6 Claims, 6 Drawing Sheets

Specification includes a Sequence Listing.

METHOD AND DEVICE FOR IDENTIFYING SPECIFIC REGION IN MICROORGANISM TARGET FRAGMENT AND USE THEREOF

CROSS REFERENCE TO RELATED PATENT APPLICATION

The present application is the US national stage of PCT/CN2020/090180 filed on 2020 May 14, which claims the priority of the Chinese patent application No. 202010254403.4 filed on 2020 Apr. 2, which application is incorporated herein by reference.

TECHNICAL FIELD

The present disclosure relates to the field of bioinformatics, and in particular, to a method and a device for identifying specific regions in microorganism target fragments and a use thereof.

BACKGROUND

DNA concentrations of pathogenic microorganisms in biological samples are mostly very low and close to the detection limit. Traditional Polymerase Chain Reaction (PCR) or real-time PCR is often lack of detection sensitivity. Other methods such as two-step nested PCR may have better sensitivity. However, these methods are time-consuming, costly, and have poor accuracy. Therefore, it is important to improve the detection sensitivity. One way is to find a suitable template region when designing primers and probes. Usually, plasmids and 16S rRNA are used.

However, using plasmids for primer design would cause some problems: Not all microorganisms contain species-specific plasmids. Some microorganisms even have no plasmids. First of all, the species specificity of plasmid DNA is uncertain. The sequences on plasmids of some species are highly similar to those on plasmids of other species. Therefore, plasmid-based PCR tests are at a high risk of producing false positive or false negative results. Many clinical laboratories still need to use other PCR primer pairs for confirmatory experiments. Secondly, plasmids are not universal. Some species do not have plasmids, so it is not possible to use plasmids to detect the species, let alone to design primers on plasmids to improve the detection sensitivity. For example, studies have reported that about 5% of *Neisseria gonorrhoeae* strains cannot be detected since they lack plasmids.

Similarly, using rRNA gene regions as templates for PCR detection also has some problems: although rRNA genes exist in the genomes of all microbial species, and there are often multiple copies that can improve detection sensitivity. In fact, not all rRNA genes are specific. For example, there is only one copy of rRNA gene in *Mycobacterium tuberculosis* H37Rv. In addition, some changes in rRNA gene sequence are not suitable for detection. For example, between closely related species or even between strains of different subtypes of the same species, rRNA genes cannot meet the requirements of species specificity or even subspecies specificity because the sequence of rRNA genes is too conservative.

SUMMARY

The present disclosure provides a method and a device for identifying specific regions in microorganism target fragments and a use thereof.

A first aspect of the present disclosure provides a method for identifying a specific region in a microorganism target fragment, which includes at least the following operations:

S100, respectively comparing a microorganism target fragment with whole genome sequences of one or more comparison strains one-to-one, and removing fragments of which a similarity exceeds a preset value, to obtain a plurality of residual fragments as first-round cut fragments $T_1$-$T_n$, wherein n is an integer greater than or equal to 1;

S200, respectively comparing the first-round cut fragments $T_1$-$T_n$ with whole genome sequences of the remaining comparison strains, and removing fragments of which the similarity exceeds a preset value, to obtain a collection of residual cut fragments as a candidate specific region of the microorganism target fragment; and S300, verifying and obtaining a specific region: determining whether the candidate specific region meets the following requirements:
1) searching in public databases to find whether there are other species of which a similarity to the candidate specific region is greater than the preset value;
2) respectively comparing the candidate specific region with whole genome sequences of the comparison strains and a whole genome sequence of a host of a source strain of the microorganism target fragment, to find whether there are fragments with a similarity greater than the preset value;

if the candidate specific region does not meet the above requirements, the candidate specific region is a specific region of the microorganism target fragment.

A second aspect of the present disclosure provides a device for identifying a specific region in a microorganism target fragment, which includes at least the following modules:

a first-round cut fragment obtaining module, configured to respectively compare a microorganism target fragment with whole genome sequences of one or more comparison strains one-to-one, and remove fragments of which a similarity exceeds a preset value, to obtain a plurality of residual fragments as first-round cut fragments $T_1$-$T_n$, wherein n is an integer greater than or equal to 1;

a candidate specific region obtaining module, configured to respectively compare the first-round cut fragments $T_1$-$T_n$ with whole genome sequences of remaining comparison strains, and remove fragments of which the similarity exceeds a preset value, to obtain a collection of residual cut fragments as candidate specific regions of the microorganism target fragment; and a specific region verifying and obtaining module, configured to determine whether the candidate specific region meets the following requirements:
1) searching in public databases to find whether there are other species of which a similarity to the candidate specific region is greater than the preset value;
2) respectively comparing the candidate specific region with whole genome sequences of the comparison strains and a whole genome sequence of a host of a source strain of the microorganism target fragment, to find whether there are fragments with a similarity greater than the preset value;

if the candidate specific region does not meet the above requirements, the candidate specific region is a specific region of the microorganism target fragment.

A third aspect of the present disclosure provides a computer readable storage medium, which stores a computer program. When executed by a processor, the program implements the above-mentioned method for identifying a specific region in a microorganism target fragment.

A fourth aspect of the present disclosure provides a computer processing device, including a processor and the above-mentioned computer readable storage medium. The processor executes the computer program on the computer readable storage medium to implement the operations of the above-mentioned method for identifying a specific region in a microorganism target fragment.

A fifth aspect of the present disclosure provides an electronic terminal, including a processor, a memory and a communicator; the memory stores a computer program, the communicator communicates with an external device, and the processor executes the computer program stored in the memory, so that the electronic terminal executes the above-mentioned method for identifying a specific region in a microorganism target fragment.

The present disclosure provides a use of the above-mentioned method for identifying a specific region in a microorganism target fragment, the above-mentioned device for identifying a specific region in a microorganism target fragment, the above-mentioned computer readable storage medium, the above-mentioned computer processing device, or the above-mentioned electronic terminal for identifying a specific region in a microorganism target fragment.

As described above, the method and the device for identifying a specific region in a microorganism target fragment and the use thereof according to the present disclosure have the following beneficial effects:

Compared with the literature database, the test case of the present disclosure has higher accuracy; the sensitivity is high, and the subspecies level can be identified; a dual-verification module is provided, and the result is accurate. When using plasmids to detect specificity, there will be the following problems: not all plasmids have species specificity and universality; when using rRNA to detect specificity, there will be the following problems: some rRNA genes in the same species cannot be distinguished from each other. The present disclosure is capable of detecting species-specific and even subspecies-specific target fragments. The present disclosure is not limited to whether there is a genome annotation. What's needed is merely to provide the names of the target strains or to upload sequence files locally. The present disclosure may cover all pathogenic microorganisms, including bacteria, virus, fungi, amoebas, cryptosporidia, *flagellates*, microsporidia, piroplasma, plasmodia, toxoplasmas, *trichomonas* and kinetoplastids.

DETAILED DESCRIPTION OF THE PREFERRED EMBODIMENTS

The embodiments of the present disclosure will be described below. Those skilled in the art can easily understand other advantages and effects of the present disclosure according to contents disclosed by the specification. The present disclosure may also be implemented or applied through other different specific implementation modes. Various modifications or changes may be made to all details in the specification based on different points of view and applications without departing from the spirit of the present disclosure.

In addition, it should be understood that one or more method operations mentioned in the present disclosure are not exclusive of other method operations that may exist before or after the combined operations or that other method operations may be inserted between these explicitly mentioned operations, unless otherwise stated. It should also be understood that the combined connection relationship between one or more operations mentioned in the present disclosure does not exclude that there may be other operations before or after the combined operations or that other operations may be inserted between these explicitly mentioned operations, unless otherwise stated. Moreover, unless otherwise stated, the numbering of each method step is only a convenient tool for identifying each method step, and is not intended to limit the order of each method step or to limit the scope of the present disclosure. The change or adjustment of the relative relationship shall also be regarded as the scope in which the present disclosure may be implemented without substantially changing the technical content.

Please refer to FIG. 1A to FIG. 3. It needs to be stated that the drawings provided in the following embodiments are just used for schematically describing the basic concept of the present disclosure, thus only illustrating components only related to the present disclosure and are not drawn according to the numbers, shapes and sizes of components during actual implementation, the configuration, number and scale of each component during actual implementation thereof may be freely changed, and the component layout configuration thereof may be more complicated.

Figure 1A:
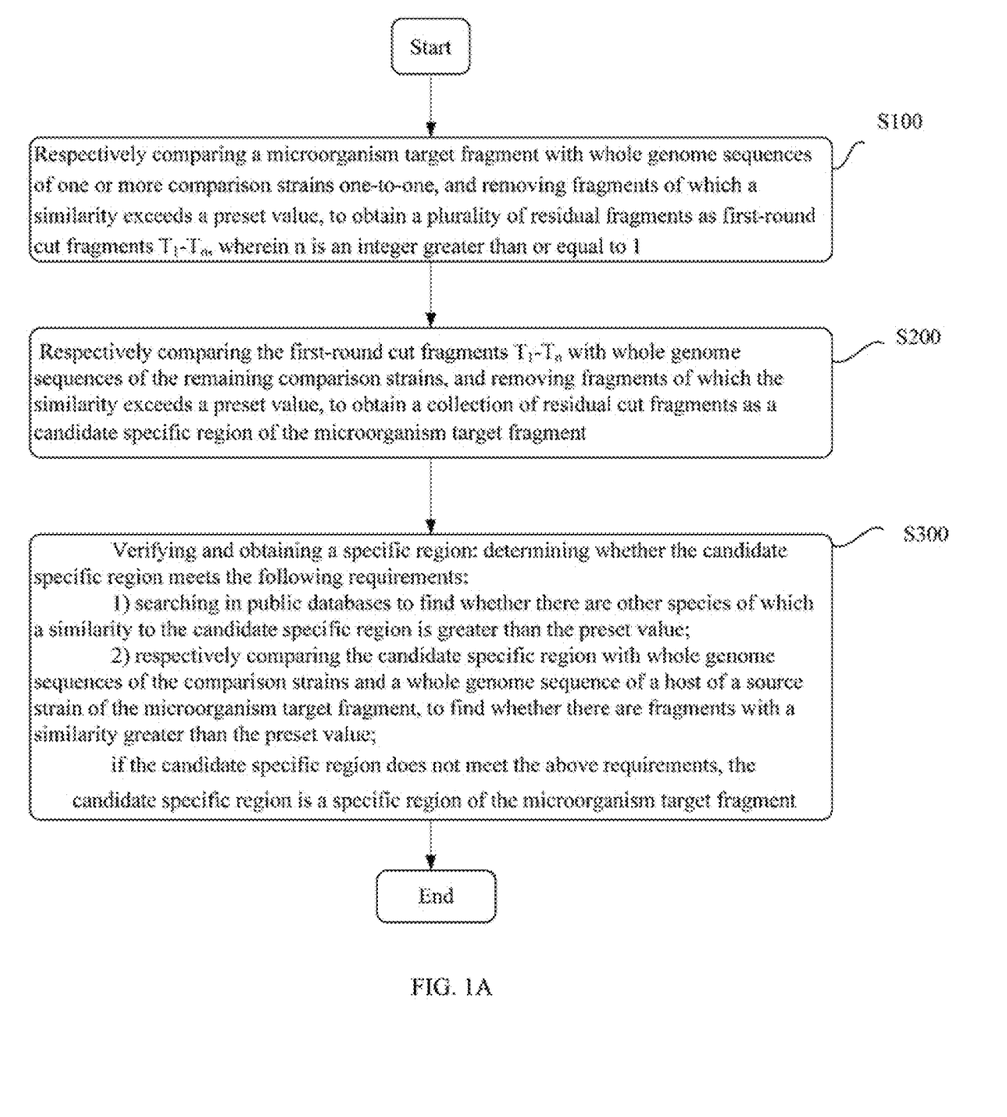
FIG. 1A is a flow chart of a method according to an embodiment of the present disclosure.

As shown in FIG. 1A, the method for identifying a specific region in a target sequence according to an embodiment of the present disclosure includes at least the following operations:

S100, respectively comparing a microorganism target fragment with whole genome sequences of one or more comparison strains one-to-one, and removing fragments of which a similarity exceeds a preset value, to obtain a plurality of residual fragments as first-round cut fragments $T_1$-$T_n$, wherein n is an integer greater than or equal to 1;

S200, respectively comparing the first-round cut fragments $T_1$-$T_n$ with whole genome sequences of the remaining comparison strains, and removing fragments of which the similarity exceeds a preset value, to obtain a collection of residual cut fragments as a candidate specific region of the microorganism target fragment; and S300, verifying and obtaining a specific region: determining whether the candidate specific region meets the following requirements:

1) searching in public databases to find whether there are other species of which a similarity to the candidate specific region is greater than the preset value;
2) respectively comparing the candidate specific region with whole genome sequences of the comparison strains and a whole genome sequence of a host of a source strain of the microorganism target fragment, to find whether there are fragments with a similarity greater than the preset value;

if the candidate specific region does not meet the above requirements, the candidate specific region is a specific region of the microorganism target fragment.

The method of the present disclosure is capable of distinguishing whether the source strain of the microorganism target fragment and the comparison strains belong to the same species or the same subspecies.

In the above operations, the similarity refers to a product of a coverage rate and a matching rate of the microorganism target fragment.

The coverage rate=(length of similar sequence fragment/(end value of the microorganism target fragment-starting value of the microorganism target fragment+1)) %;

The matching rate refers to the identity value when the microorganism target fragment is compared with the comparison strain. The identity value of the two compared sequences may be obtained by software such as needle, water or blat.

The length of similar sequences refers to the number of bases that the matched fragment occupies in the target fragment when two sequences are compared, that is, the length of the matched fragment.

The preset value of the similarity may be determined as needed. The higher the preset value of the similarity, the fewer fragments will be removed. The recommended preset value of the similarity should exceed 95%, such as 96%, 97%, 98%, 99% or 100%.

Figure 1B:
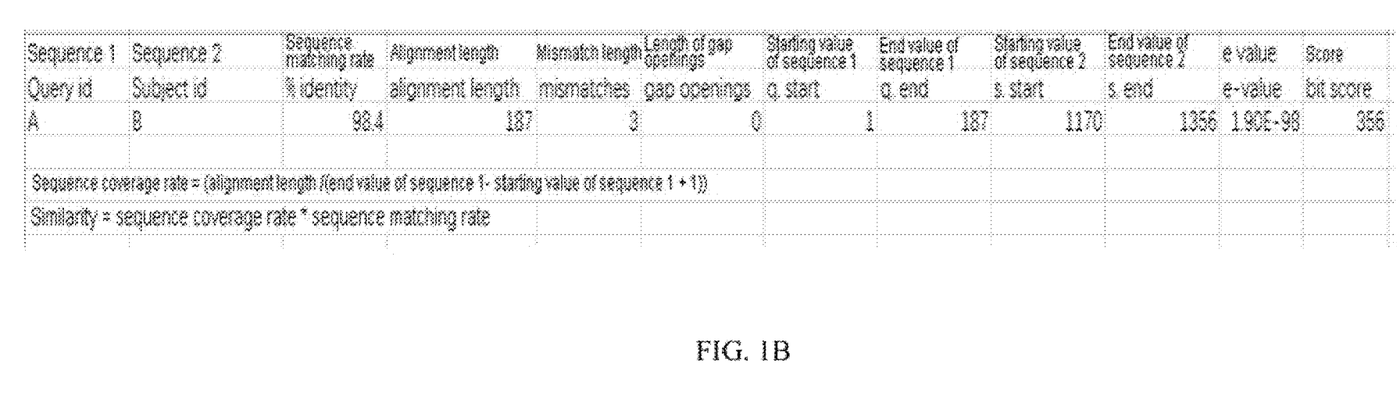
FIG. 1B is a graph showing calculation results of a coverage rate and sequence matching rate of aligned sequences.
Figure 1C:
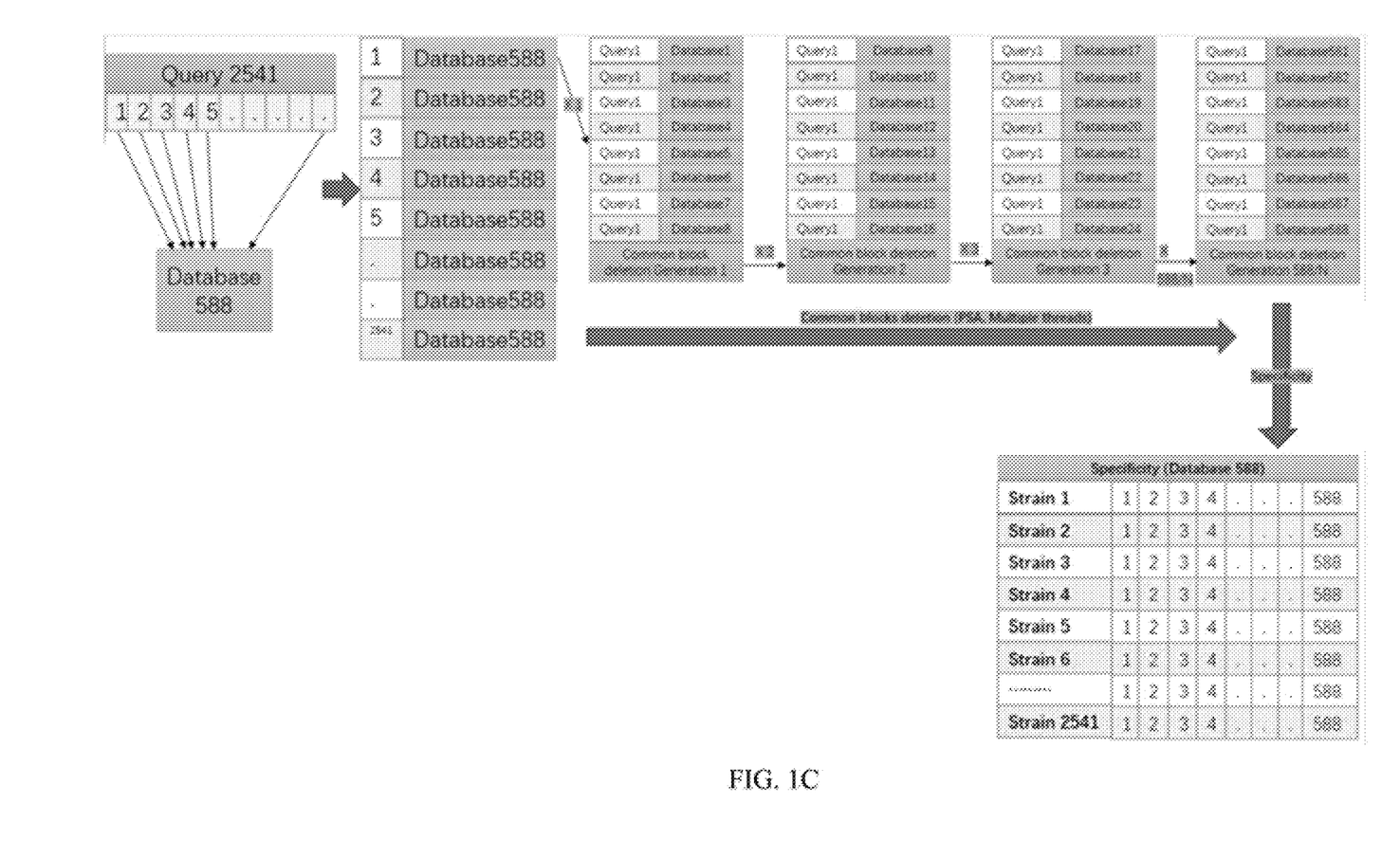
FIG. 1C is a schematic diagram showing a method of comparing a first-round cut fragment $T_n$ with whole genome sequences of remaining comparison strains by group iteration according to the present disclosure.
Figure 1D:
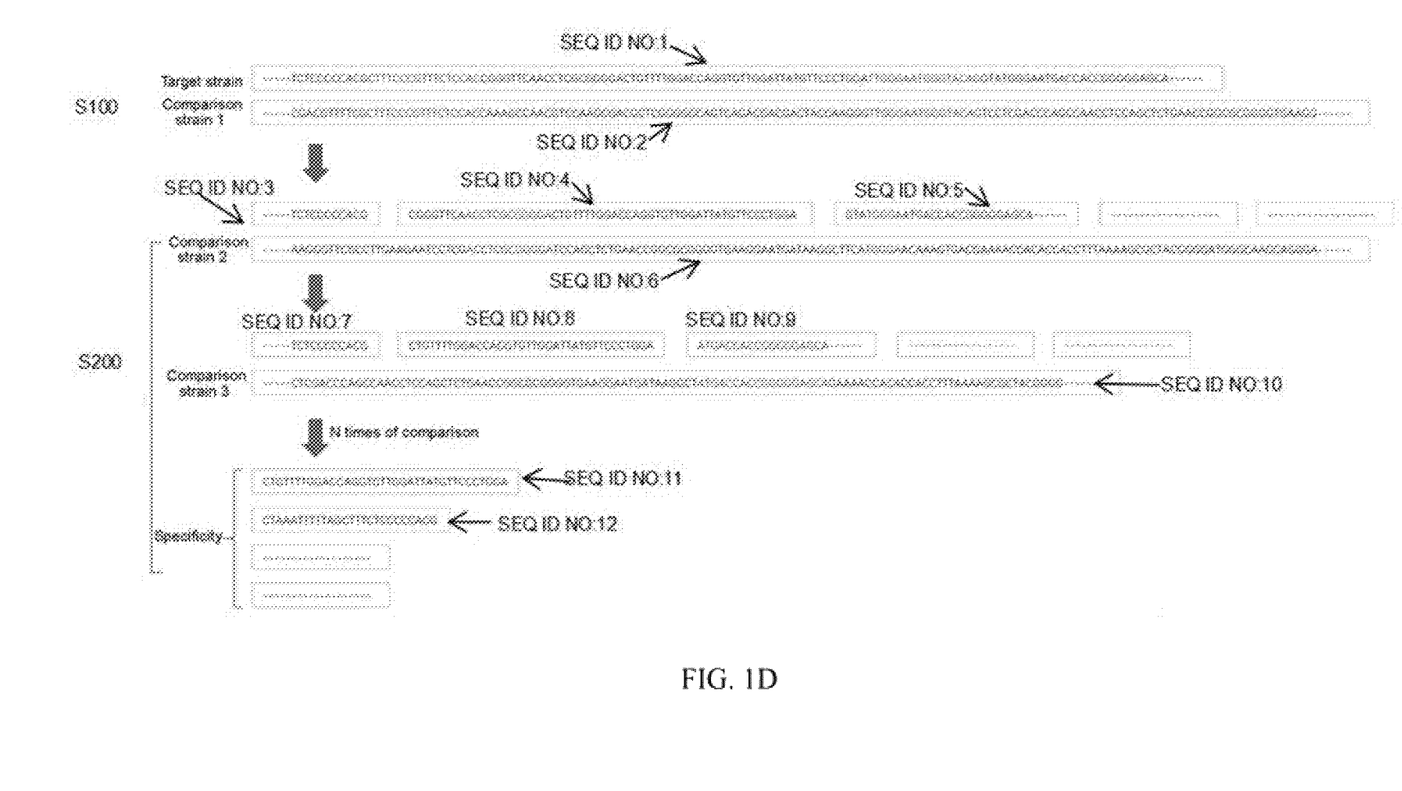
FIG. 1D is a schematic diagram showing the sequence display of a method according to an embodiment of the present disclosure.

The specific sequence is shown in operation S100 in FIG. 1D, and the light-colored bases represent sequence fragments of which the similarity exceeds the preset value.

The coverage rate and matching rate of microorganism target fragments may be calculated by software such as needle, water or blat.

For example, a calculation result is shown in FIG. 1B. Sequence A is a microorganism target fragment, sequence B is the comparison strain 1. Sequences A and B are compared.

Coverage rate of sequence A=(187/(187-1+1))*100%= 100%

The matching rate of sequence A and sequence B is equal to 98.4%.

Then the similarity between A and B=100%*98.4%= 98.4%.

The microorganism target fragment and the comparison strains in operation S100 are all derived from public databases, which are mainly selected from NCBI.

Further, the method includes the following operations: S110, comparing the selected adjacent microorganism target fragments in pairs; if the similarity after comparison is lower than the preset value, issuing an alarm and displaying the screening conditions corresponding to the target strain.

Abnormal data caused by human errors or other reasons can be filtered. The microorganism target fragment in operation S100 may be a whole genome of a microorganism or a gene fragment of a microorganism.

In operation S200, in order to speed up the comparison, in a preferred embodiment, the first-round cut fragments $T_1$-$T_n$ are respectively compared with whole genome sequences of the remaining comparison strains by group iteration.

Specifically, as shown in FIG. 1C, the first-round cut fragment $T_n$ being compared with whole genome sequences of the remaining comparison strains by group iteration includes the following operations:

dividing the remaining comparison strains into P groups, each group including a plurality of comparison strains;

simultaneously comparing the first-round cut fragment $T_n$ with the whole genome sequences of each comparison strain in the first group one-to-one, and removing fragments of which the similarity exceeds the preset value, to obtain a plurality of residual fragments as a first-round candidate sequence library of the first-round cut fragment $T_n$;

simultaneously comparing a previous-round candidate sequence library of the first-round cut fragment $T_n$ with whole genome sequences of each comparison strain in the next group one-to-one, and removing fragments of which the similarity exceeds the preset value, to obtain a plurality of residual fragments as a next-round candidate sequence library of the first-round cut fragment $T_n$; repeating operation S212 from the first-round candidate sequence library until a Pth-round candidate sequence library is obtained as a candidate specific sequence library of the first-round cut fragment $T_n$;

a collection of all the candidate specific sequence libraries of the first-round cut fragments is the candidate specific region.

In order to avoid multi-thread blocking, the number of comparison strains contained in a comparison strain group should be set according to the hardware configuration of the computing environment. The number may be the number of threads set according to the total configuration of the operating environment. Generally, the number of threads may be 1-50. Specifically, the number of threads may be 1-4, 4-8, 8-10, 10-20, or 20-50. Preferably, the number of threads is 4. In the embodiment shown in FIG. 1C, the number of threads is 8.

For example, as shown in FIG. 1C, the target sequence contains 2541 microorganism target fragments, the number of the comparison strains is 588, m=8. First, simultaneously comparing the microorganism target fragment 1 with the sequences 1-8 in the 588 comparison strains, performing the first-round cutting to remove the matched sequences, and obtaining the first-round specific sequence library after a comprehensive summary; then, simultaneously comparing the first-round specific sequence library with the sequences 9-16 in the 588 comparison strains, performing the second-round cutting to remove the matched sequences, and obtaining the second-round specific sequence library after a comprehensive summary; then, simultaneously comparing the second-round specific sequence library with the sequences 17-24 in the 588 comparison strains, performing the third-round cutting to remove the matched sequences, and obtaining the third-round specific sequence library after a comprehensive summary; . . . , performing sequentially, until the 73th-round specific sequence library is simultaneously compared with the sequences 585-588 in the 588 comparison strains, the matched sequences is removed by performing the 74th-round cutting, and the 74th-round specific sequence library, i.e., the specific sequence library of the target fragment 1, is obtained after a comprehensive summary.

Secondly, simultaneously comparing the microorganism target fragment 2 in the target sequence with the sequences 1-8 in the 588 comparison strains, performing the first-round cutting to remove the matched sequences, and obtaining the first-round specific sequence library after a comprehensive summary; then, simultaneously comparing the first-round specific sequence library with the sequences 9-16 in the 588 comparison strains, performing the second-round cutting to remove the matched sequences, and obtaining the second-round specific sequence library after a comprehensive summary; then, simultaneously comparing the second-round specific sequence library with the sequences 17-24 in the 588 comparison strains, performing the third-round cutting to remove the matched sequences, and obtaining the third-round specific sequence library after a comprehensive summary; . . . , performing sequentially, until the 73th-round specific sequence library is simultaneously compared with the sequences 585-588 in the 588 comparison strains, the matched sequences is removed by performing the 74th-round cutting, and the 74th-round specific sequence library, i.e., the specific sequence library of the target fragment 2, is obtained after a comprehensive summary.

Performing sequentially, until the comparison of the microorganism target fragment 2541 in the target sequence and the 588 comparison strains are completed. The cut fragments obtained are the candidate specific regions of the microorganism target fragments.

In a preferred embodiment, the operation S200 further includes:

performing operations S100 and S200 to obtain candidate specific regions of each microorganism target fragment in the target sequence, taking a collection of the candidate specific regions of each microorganism target fragment as candidate specific regions of the target sequence.

The target sequence may include multiple target fragments. The multiple target fragments may be fragments obtained by screening from the genome of microorganisms through other screening operations, for example, multi-copy fragments of specific microorganisms.

In operation S300, the public databases are mainly selected from NCBI The algorithm for searching in the public database may be the blast algorithm.

Further, before performing operations S100, S200 and S300, the cutting size is set according to the hardware configuration of the computing environment, and the data to be calculated is cut in units. Specifically, in operation S100, the data to be calculated is the target fragments. In operation S200, the data to be calculated is the current-round specific sequence library after removing the matched sequences in each iteration. In operation S300, the data to be calculated is the candidate specific region.

After cutting in units, the number of units * the configuration required to run a unit file cannot exceed the total configuration of the operating environment.

Cutting in units refers to dividing the total number of the to-be-cut sequences by the number of threads, and m is recorded as the number of units after cutting in units. Each thread runs the same number of computing tasks in a multi-thread operating environment to ensure efficient computing under optimal performance conditions.

Figure 2:
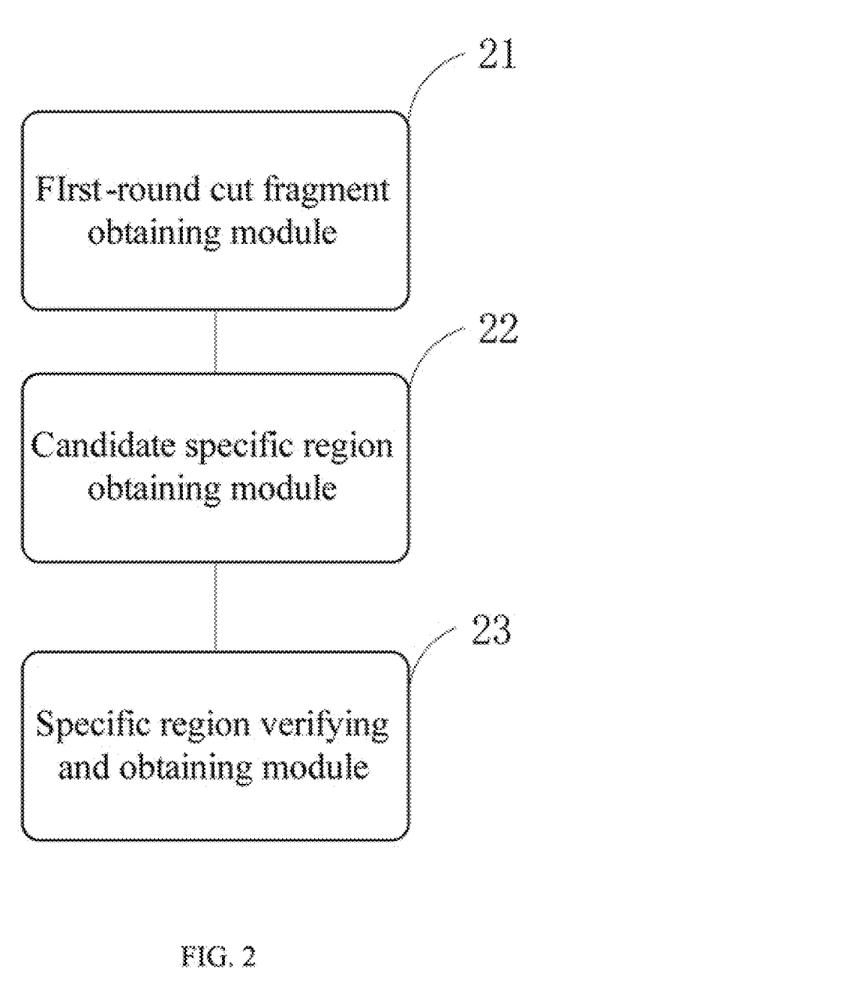
FIG. 2 is a schematic diagram of a device according to an embodiment of the present disclosure.

As shown in FIG. 2, the device for identifying a specific region in a microorganism target fragment according to the embodiment of the present disclosure includes at least the following modules:

a first-round cut fragment obtaining module 21, configured to respectively compare a microorganism target fragment with whole genome sequences of one or more comparison strains one-to-one, and remove fragments of which a similarity exceeds a preset value, to obtain a plurality of residual fragments as first-round cut fragments $T_1$-$T_n$, wherein n is an integer greater than or equal to 1;

a candidate specific region obtaining module 22, configured to respectively compare the first-round cut fragments $T_1$-$T_n$ with whole genome sequences of remaining comparison strains, and remove fragments of which the similarity exceeds a preset value, to obtain a collection of residual cut fragments as candidate specific regions of the microorganism target fragment; and a specific region verifying and obtaining module 23, configured to determine whether the candidate specific region meets the following requirements:
1) searching in public databases to find whether there are other species of which a similarity to the candidate specific region is greater than the preset value;
2) respectively comparing the candidate specific region with whole genome sequences of the comparison strains and a whole genome sequence of a host of a source strain of the microorganism target fragment, to find whether there are fragments with a similarity greater than the preset value;

if the candidate specific region does not meet the above requirements, the candidate specific region is a specific region of the microorganism target fragment.

The device of the present disclosure is capable of distinguishing whether the source strain of the microorganism target fragment and the comparison strain belong to the same species or the same subspecies.

The similarity refers to a product of a coverage rate and a matching rate of the target fragment. The coverage rate= (length of similar sequence fragment/(end value of the microorganism target fragment-starting value of the microorganism target fragment+1)) %.

In the candidate specific region obtaining module, the first-round cut fragments $T_1$-$T_n$ are respectively compared with whole genome sequences of the remaining comparison strains by group iteration.

When the first-round cut fragment $T_n$ is compared with whole genome sequences of the remaining comparison strains by group iteration, the candidate specific region obtaining module includes the following submodules:

a comparison strain grouping submodule, configured to divide the remaining comparison strains into P groups, each group including a plurality of comparison strains;

a first-round candidate sequence library obtaining submodule, configured to simultaneously compare the first-round cut fragment $T_n$ with the whole genome sequences of each comparison strain in the first group one-to-one, and remove fragments of which the similarity exceeds the preset value, to obtain a plurality of residual fragments as a first-round candidate sequence library of the first-round cut fragment $T_n$;

a candidate specific region obtaining submodule, to simultaneously compare a previous-round candidate sequence library of the first-round cut fragment $T_n$ with whole genome sequences of each comparison strain in a next group one-to-one, and remove fragments of which the similarity exceeds the preset value, to obtain a plurality of residual fragments as a next-round candidate sequence library of the first-round cut fragment $T_n$; the candidate specific region obtaining submodule is repeated from the first-round candidate sequence library until a Pth-round candidate sequence library is obtained as a candidate specific sequence library of the first-round cut fragment $T_n$;

a collection of all the candidate specific sequence libraries of the first-round cut fragments is the candidate specific region.

The number of comparison strains contained in a comparison strain group is set according to the hardware configuration of the computing environment.

In an embodiment, the device further includes:

a candidate specific region obtaining module of the target sequence, which executes the first-round cut fragment obtaining module of the target fragment and the candidate specific region obtaining module of the target fragment to obtain candidate specific regions of each target fragment in the target sequence, and takes a collection of the candidate specific regions of each target fragments as candidate specific regions of the target sequence.

Optionally, the first-round cut fragment obtaining module further includes the following submodules: a raw data similarity comparison submodule, to compare the selected adjacent microorganism target fragments in pairs; if the similarity after comparison is lower than the preset value, an alarm is issued and the screening conditions corresponding to the target strain are displayed.

Since the principles of the device in the present embodiment is basically the same as that of the above-mentioned method embodiment, the definitions of the same features, the calculation methods, the enumeration of the embodiments, and the enumeration of the preferred embodiments may be used interchangeably, thus will not be described again.

It should be noted that the division of each module of the above apparatus is only a division of logical functions. In actual implementation, the modules may be integrated into one physical entity in whole or in part, or may be physically separated. These modules may all be implemented in the form of processing component calling by software. These modules may also be implemented entirely in hardware. It is also possible that some modules are implemented in the form of processing component calling by software, and some modules are implemented in the form of hardware. For example, the obtaining module may be a separate processing element, or may be integrated into a chip, or may be stored in a memory in the form of program code. The function of the above obtaining module is called and executed by one of the processing elements. The implementation of other modules is similar. In addition, all or part of these modules may be integrated or implemented independently. The processing elements described herein may be an integrated circuit with signal processing capabilities. In the implementation process, each operation of the above method or each of the above modules may be implemented by an integrated logic circuit of hardware in the processor element or instruction in a form of software.

For example, the above modules may be one or more integrated circuits configured to implement the above method, such as one or more application specific integrated circuits (ASIC), or one or more digital signal processors (DSP), or one or more field programmable gate arrays (FPGA), or graphics processing unit (GPU). As another example, when one of the above modules is implemented in the form of calling program codes of a processing element, the processing element may be a general processor, such as a central processing unit (CPU) or other processors that may call program codes. As another example, these modules may be integrated and implemented in the form of a system-on-a-chip (SOC).

Some embodiments of the present disclosure further provide a computer readable storage medium, which stores a computer program. When executed by a processor, the program implements the above-mentioned method for identifying specific regions in microorganism target fragments.

Some embodiments of the present disclosure provide a computer processing device, including a processor and the above-mentioned computer readable storage medium. The processor executes the computer program on the computer readable storage medium to implement the operations of the above-mentioned method for identifying specific regions in microorganism target fragments.

Some embodiments of the present disclosure provide an electronic terminal, including a processor, a memory and a communicator; the memory stores a computer program, the communicator communicates with an external device, and the processor executes the computer program stored in the memory, so that the electronic terminal executes and implements the above-mentioned method for identifying specific regions in microorganism target fragments.

Figure 3:
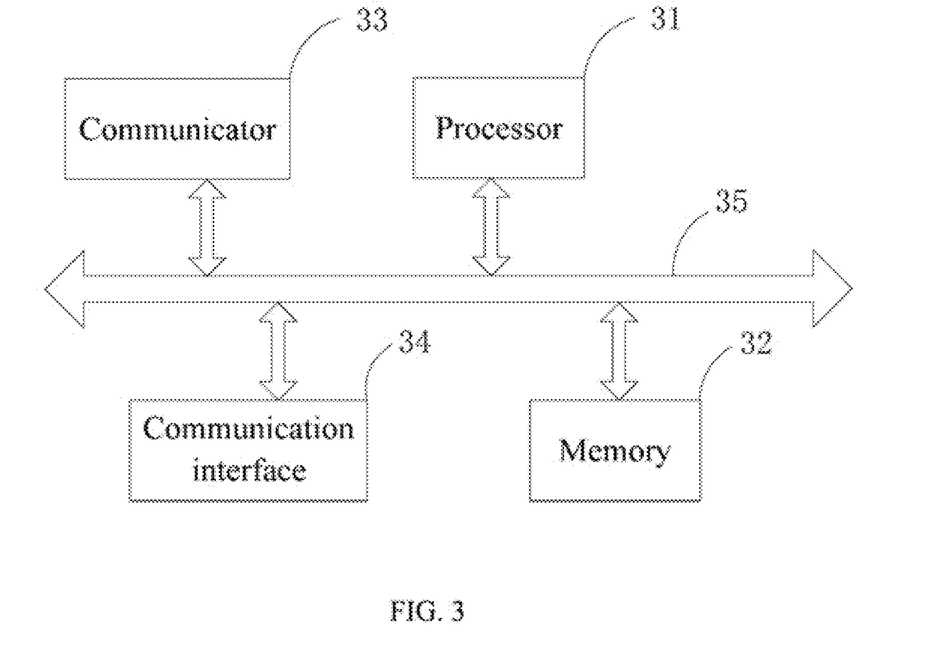
FIG. 3 is a schematic diagram of an electronic terminal according to an embodiment of the present disclosure.

FIG. 3 is a schematic diagram showing the electronic terminal provided by the present disclosure. The electronic terminal includes a processor 31, a memory 32, a communicator 33, a communication interface 34 and a system bus 35; the memory 32 and the communication interface 34 are connected and communicated with the processor 31 and the communicator 33 through the system bus 35. The memory 32 is used to store computer programs. The communicator 33 and the communication interface 34 are used to communicate with other devices. The processor 31 and the communicator 33 are used to execute the computer program, so that the electronic terminal performs the operations of the above method for identifying specific regions in microorganism target fragments.

The system bus mentioned above may be a peripheral component interconnect (PCI) bus or an extended industry standard architecture (EISA) bus, etc. The system bus may include address bus, data bus, control bus and so on. For convenience of representation, only a thick line is used in the figure, but it does not mean that there is only one bus or one type of bus. The communication interface is used to implement communication between the database access device and other devices (such as a client, a read-write library, and a read-only library). The memory may include a random access memory (RAM), or may also include a non-volatile memory, such as at least one disk memory.

The above-mentioned processor may be a general processor, including a central processing unit (CPU), a network processor (NP), and the like. The above-mentioned processor may also be a digital signal processor (DSP), an application specific integrated circuit (ASIC), a field-programmable gate array (FPGA), a graphics processing unit (GPU) or other programmable logic devices, discrete gate or transistor logic devices, or discrete hardware components.

Those of ordinary skill will understand that all or part of the operations to implement the various method embodiments described above may be accomplished by hardware associated with a computer program. The computer program may be stored in a computer readable storage medium. The program, when executed, performs the operations including the above method embodiments. The computer readable storage mediums may include, but are not limited to, floppy disks, optical disks, compact disc read-only memories (CD-ROM), magneto-optical disks, read only memories (ROM), random access memories (RAM), erasable programmable read-only memory (EPROM), electrically erasable programmable read-only memory (EEPROM), magnetic cards or optical cards, flash memories, or other types of medium or machine-readable media suitable for storing machine-executable instructions. The computer readable storage medium may be a product that is not accessed to a computer device, or a component that has been accessed to a computer device for use.

In terms of specific implementation, the computer programs may be routines, programs, objects, components, data structures or the like that perform specific tasks or implement specific abstract data types.

The above-mentioned method for identifying a specific region in a microorganism target fragment, the device for identifying a specific region in a microorganism target fragment, the computer readable storage medium, the computer processing device or the electronic terminal may be used in the PCR detection of microorganisms, and specifically, in the screening of template sequences.

The present disclosure provides a use of the above-mentioned method for identifying a specific region in a microorganism target fragment, the above-mentioned device for identifying a specific region in a microorganism target fragment, the above-mentioned computer readable storage medium, the above-mentioned computer processing device, or the above-mentioned electronic terminal for identifying a specific region in a microorganism target fragment.

The use is to distinguish whether the source strain of the microorganism target fragment and the comparison strain belong to the same species or the same subspecies.

The microorganism includes one or more of bacterium, virus, fungus, amoeba, *cryptosporidium*, flagellate, microsporidium, piroplasma, *plasmodium, toxoplasma, trichomonas* and kinetoplastid.

The above-mentioned embodiments are merely illustrative of the principle and effects of the present disclosure instead of limiting the present disclosure. Modifications or variations of the above-described embodiments may be made by those skilled in the art without departing from the spirit and scope of the disclosure. Therefore, all equivalent modifications or changes made by those who have common knowledge in the art without departing from the spirit and technical concept disclosed by the present disclosure shall be still covered by the claims of the present disclosure.

The content of the following submission on ASCII text file is incorporated herein by reference in its entirety: a computer readable form (CRF) of the Sequence Listing (file name: 210054 sequence listing ST25, date recorded: Dec. 28, 2022, size: 44 KB).

The invention claimed is:

1. A method for identifying presence of a microorganism in a sample, comprising:
   identifying a specific region in a microorganism target fragment, at least comprising:
   (S100), respectively comparing the microorganism target fragment with whole genome sequences of one or more comparison strains one-to-one, and removing fragments in the microorganism target fragment of which a similarity exceeds a preset value, to obtain one or more residual fragments as first-round cut fragments $T_1$-$T_n$, wherein n is an integer greater than or equal to 1; then
   (S200), respectively comparing the first-round cut fragments $T_1$-$T_n$ with whole genome sequences of a second plurality of comparison strains, and removing subfragments of the first-round cut fragments of which a similarity exceeds the preset value, to obtain a collection of residual cut fragments as candidate specific regions of the microorganism target fragment; and then
   (S300), verifying and obtaining a specific region, comprising: determining whether each candidate specific region meets the following requirements:
   1) Searching in public databases to find whether there are species other than the species of the microorganism of the microorganism target fragment of which a similarity to the candidate specific region is greater than the preset value;
   2) Respectively comparing the candidate specific region with whole genome sequences of the one or more comparison strains and the second plurality of comparison strains and a whole genome sequence of a host of a source strain of the microorganism target fragment, to find whether there are fragments with a similarity greater than the preset value;
   if the candidate specific region does not meet the above requirements, the candidate specific region is a specific region of the microorganism target fragment; and performing a PCR amplification of the specific region to detect the microorganism.

2. The method according to claim 1:
   a) wherein the method is capable of distinguishing whether the source strain of the microorganism target fragment and a comparison strain belong to a same species or a same subspecies;
   b) wherein each similarity refers to a product of a coverage rate and a matching rate of the microorganism target fragment, and the coverage rate=(length of similar sequence fragment/(end value of the microorganism target fragment-starting value of the microorganism target fragment+1)) %;
   c) wherein in operation (S200), the first-round cut fragments $T_1$-$T_n$ are respectively compared with whole genome sequences of the second plurality of comparison strains by group iteration;
   d) wherein operation (S100) further comprises the following operation: (S110), comparing selected adjacent microorganism target fragments in pairs; and if the similarity after comparison is lower than the preset value, issuing an alarm and displaying screening conditions corresponding to a target strain; or
   any combination thereof.

3. The method according to claim 2, wherein the comparing the first-round cut fragment $T_n$ with whole genome sequences of the second plurality of comparison strains by group iteration includes the following operations:
   (S210), dividing the second plurality of comparison strains into P groups, each group including a plurality of comparison strains;
   (S211), simultaneously comparing the first-round cut fragment $T_n$ with the whole genome sequences of each comparison strain in the first group one-to-one, and removing subfragments of the first-round cut fragment $T_n$ of which the similarity exceeds the preset value, to obtain a plurality of residual fragments as a first-round candidate sequence library of the first-round cut fragment $T_n$; and
   (S212), simultaneously comparing a previous-round candidate sequence library of the first-round cut fragment $T_n$ with whole genome sequences of each comparison strain in the next group one-to-one, and removing subfragments of the previous-round candidate sequence library of which the similarity exceeds the preset value, to obtain a plurality of residual fragments as a next-round candidate sequence library of the first-round cut fragment $T_n$; repeating operation (S212) from the first-round candidate sequence library until a Pth-round candidate sequence library is obtained as a candidate specific sequence library of the first-round cut fragment $T_n$; wherein a collection of all the candidate specific sequence libraries of the first-round cut fragments are the candidate specific regions.

4. The method according to claim 3, wherein a number of comparison strains contained in a comparison strain group is set according to a hardware configuration of a computing environment.

5. The method according to claim 1, further comprising: after operation (S200), performing operations (S100) and (S200) to obtain candidate specific regions of each microorganism target fragment in a target sequence, taking a collection of the candidate specific regions of each microorganism target fragment as candidate specific regions of the target sequence.

6. The method according to claim 1, wherein the microorganism includes one or more of bacterium, virus, fungus, amoeba, *cryptosporidium*, flagellate, microsporidium, piroplasma, *plasmodium, toxoplasma, trichomonas* and kinetoplastid.

* * * * *

SEQUENCE LISTING

```
<160> NUMBER OF SEQ ID NOS: 12

<210> SEQ ID NO 1
<211> LENGTH: 126
<212> TYPE: DNA
<213> ORGANISM: Artificial Sequence
<220> FEATURE:
<223> OTHER INFORMATION: Target strain

<400> SEQUENCE: 1
tctcccccac gctttcccgt ttctccaccg ggttcaacct cgcggggact gttttggacc      60
aggtgttgga ttatgttccc tggattggga atgggtacag gtatgggaat gaccaccggg     120
ggagca                                                                126

<210> SEQ ID NO 2
<211> LENGTH: 145
<212> TYPE: DNA
<213> ORGANISM: Artificial Sequence
<220> FEATURE:
<223> OTHER INFORMATION: Comparison strain 1

<400> SEQUENCE: 2
cgacgttttc gctttcccgt ttctccacca aagccaacgt ccaagcgacg ctcgggggca      60
gtcagacgac gactaccaag ggttgggaat gggtacagtc ctcgacccag ccaacctcca     120
gctctgaacc ggcgcggggt gaagg                                           145

<210> SEQ ID NO 3
<211> LENGTH: 11
<212> TYPE: DNA
<213> ORGANISM: Artificial Sequence
<220> FEATURE:
<223> OTHER INFORMATION: One of first-round cut fragments

<400> SEQUENCE: 3
tctcccccac g                                                           11

<210> SEQ ID NO 4
<211> LENGTH: 56
<212> TYPE: DNA
<213> ORGANISM: Artificial Sequence
```

```
<220> FEATURE:
<223> OTHER INFORMATION: One of first-round cut fragments

<400> SEQUENCE: 4
cgggttcaac ctcgcgggga ctgttttgga ccaggtgttg gattatgttc cctgga          56

<210> SEQ ID NO 5
<211> LENGTH: 26
<212> TYPE: DNA
<213> ORGANISM: Artificial Sequence
<220> FEATURE:
<223> OTHER INFORMATION: One of first-round cut fragments

<400> SEQUENCE: 5
gtatgggaat gaccaccggg ggagca                                          26

<210> SEQ ID NO 6
<211> LENGTH: 144
<212> TYPE: DNA
<213> ORGANISM: Artificial Sequence
<220> FEATURE:
<223> OTHER INFORMATION: Comparison strain 2

<400> SEQUENCE: 6
aagggttcgc cttgaagaat cctcgacctc gcggggatcc agctctgaac cggcgcgggg     60
tgaaggaatg ataaggcttc atgggaacaa agtgacgaaa accacaccac ctttaaaagc    120
gctacgggga tgggcaagca ggga                                           144

<210> SEQ ID NO 7
<211> LENGTH: 11
<212> TYPE: DNA
<213> ORGANISM: Artificial Sequence
<220> FEATURE:
<223> OTHER INFORMATION: One of second-round cut fragments

<400> SEQUENCE: 7
tctcccccac g                                                          11

<210> SEQ ID NO 8
<211> LENGTH: 36
<212> TYPE: DNA
<213> ORGANISM: Artificial Sequence
<220> FEATURE:
<223> OTHER INFORMATION: One of second-round cut fragments

<400> SEQUENCE: 8
ctgttttgga ccaggtgttg gattatgttc cctgga                               36

<210> SEQ ID NO 9
<211> LENGTH: 18
<212> TYPE: DNA
<213> ORGANISM: Artificial Sequence
<220> FEATURE:
<223> OTHER INFORMATION: One of second-round cut fragments

<400> SEQUENCE: 9
atgaccaccg ggggagca                                                   18

<210> SEQ ID NO 10
<211> LENGTH: 108
<212> TYPE: DNA
<213> ORGANISM: Artificial Sequence
<220> FEATURE:
<223> OTHER INFORMATION: Comparison strain 3
```

```
<400> SEQUENCE: 10
ctcgacccag ccaacctcca gctctgaacc ggcgcggggt gaaggaatga taaggctatg        60
accaccgggg gagcagaaaa ccacaccacc tttaaaagcg ctacgggg                    108

<210> SEQ ID NO 11
<211> LENGTH: 36
<212> TYPE: DNA
<213> ORGANISM: Artificial Sequence
<220> FEATURE:
<223> OTHER INFORMATION: A specific region

<400> SEQUENCE: 11
ctgttttgga ccaggtgttg gattatgttc cctgga                                  36

<210> SEQ ID NO 12
<211> LENGTH: 26
<212> TYPE: DNA
<213> ORGANISM: Artificial Sequence
<220> FEATURE:
<223> OTHER INFORMATION: A specific region

<400> SEQUENCE: 12
ctaaattttt agctttctcc cccacg                                             26
```